(12) United States Patent
Soltz

(10) Patent No.: US 10,383,626 B2
(45) Date of Patent: *Aug. 20, 2019

(54) METHOD AND SYSTEM TO DETERMINE AN OPTIMAL TISSUE COMPRESSION TIME TO IMPLANT A SURGICAL ELEMENT

(71) Applicant: Covidien LP, Mansfield, MA (US)

(72) Inventor: Michael A. Soltz, Fairfield, CT (US)

(73) Assignee: Covidien LP, Mansfield, MA (US)

( * ) Notice: Subject to any disclaimer, the term of this patent is extended or adjusted under 35 U.S.C. 154(b) by 887 days.

This patent is subject to a terminal disclaimer.

(21) Appl. No.: 14/614,506

(22) Filed: Feb. 5, 2015

(65) Prior Publication Data

US 2015/0150554 A1 Jun. 4, 2015

Related U.S. Application Data

(60) Continuation of application No. 14/446,907, filed on Jul. 30, 2014, now Pat. No. 8,968,217, which is a
(Continued)

(51) Int. Cl.
*A61B 5/107* (2006.01)
*A61B 17/068* (2006.01)
(Continued)

(52) U.S. Cl.
CPC .......... *A61B 17/068* (2013.01); *A61B 5/1075* (2013.01); *A61B 17/072* (2013.01);
(Continued)

(58) Field of Classification Search
CPC ..... A61B 17/068; A61B 5/1075; A61B 19/46; A61B 2019/465; A61B 90/06
See application file for complete search history.

(56) References Cited

U.S. PATENT DOCUMENTS 4,315,372 A 2/1982 Kinkead
4,432,376 A 2/1984 Huszar
(Continued)

FOREIGN PATENT DOCUMENTS

EP 0435837 A1 * 7/1991 ............ A61B 6/102
EP 0552050 A2 7/1993
(Continued)

OTHER PUBLICATIONS

International Search Report from European Application EP 06 01 1501 dated Dec. 12, 2006.
(Continued)

*Primary Examiner* — Adam J Eiseman

(57) ABSTRACT

A method for determining an optimal compression of tissue to apply a surgical element to the tissue, the method comprising:
  measuring an initial thickness of the tissue before applying a load to the tissue with a moveable platen;
  applying the load to the tissue with the moveable platen;
  measuring a velocity of the moveable platen in response to the load applied to the tissue;
  providing an audible signal when the velocity of the moveable platen reaches a predetermined velocity which is indicative that about eighty percent tissue compression has been achieved representing optimal compression.

8 Claims, 15 Drawing Sheets

Related U.S. Application Data division of application No. 14/016,545, filed on Sep. 3, 2013, now Pat. No. 8,900,164, which is a division of application No. 13/285,272, filed on Oct. 31, 2011, now Pat. No. 8,551,025, which is a division of application No. 11/409,154, filed on Apr. 21, 2006, now Pat. No. 8,062,236.

(60) Provisional application No. 60/764,451, filed on Feb. 2, 2006, provisional application No. 60/764,449, filed on Feb. 2, 2006.

(51) Int. Cl.
*A61B 90/00* (2016.01)
*A61B 17/072* (2006.01)

(52) U.S. Cl.
CPC ........ *A61B 17/07207* (2013.01); *A61B 90/06* (2016.02); *A61B 2090/064* (2016.02); *A61B 2090/065* (2016.02)

(56) References Cited

U.S. PATENT DOCUMENTS

| | | | |
|---|---|---|---|
| 5,038,795 A | 8/1991 | Roush et al. | |
| 5,156,161 A | 10/1992 | Lollar | |
| 5,289,826 A | 3/1994 | Kovacevic | |
| 5,383,880 A | 1/1995 | Hooven | |
| 5,403,312 A | 4/1995 | Yates et al. | |
| 5,464,144 A | 11/1995 | Guy et al. | |
| 5,503,320 A | 4/1996 | Webster et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,533,521 A | 7/1996 | Granger | |
| 5,535,934 A | 7/1996 | Boiarski et al. | |
| 5,535,937 A | 7/1996 | Boiarski et al. | |
| 5,558,671 A | 9/1996 | Yates | |
| 5,562,239 A | 10/1996 | Boiarski et al. | |
| 5,609,607 A | 3/1997 | Hechtenberg et al. | |
| 5,665,085 A | 9/1997 | Nardella | |
| 5,667,517 A | 9/1997 | Hooven | |
| 5,713,896 A | 2/1998 | Nardella | |
| 5,735,848 A | 4/1998 | Yates et al. | |
| 5,782,397 A | 7/1998 | Koukline | |
| 5,964,394 A | 10/1999 | Robertson | |
| 5,965,880 A | 10/1999 | Wolf et al. | |
| 5,997,545 A | 12/1999 | Doherty et al. | |
| H1904 H | 10/2000 | Yates et al. | |
| 6,221,023 B1 | 4/2001 | Matsuba et al. | |
| H2037 H | 7/2002 | Yates et al. | |
| 6,436,097 B1 | 8/2002 | Nardella | |
| 6,602,252 B2 | 8/2003 | Mollenauer | |
| 6,817,508 B1 | 11/2004 | Racenet et al. | |
| 7,225,554 B2 | 6/2007 | Madsen | |
| 8,062,236 B2 * | 11/2011 | Soltz | A61B 17/068 600/587 |
| 8,968,217 B2 | 3/2015 | Soltz | |
| 2003/0130677 A1 * | 7/2003 | Whitman | A61B 17/072 606/167 |
| 2004/0143263 A1 | 7/2004 | Schechter et al. | |
| 2004/0153124 A1 | 8/2004 | Whitman | |
| 2004/0232201 A1 | 11/2004 | Wenchell et al. | |
| 2005/0020941 A1 | 1/2005 | Tarabichi | |
| 2005/0021078 A1 | 1/2005 | Vleugels et al. | |
| 2005/0067458 A1 | 3/2005 | Swayze et al. | |
| 2005/0070925 A1 | 3/2005 | Shelton et al. | |
| 2005/0070958 A1 | 3/2005 | Swayze et al. | |
| 2005/0072827 A1 | 4/2005 | Mollenauer | |
| 2005/0131390 A1 | 6/2005 | Heinrich et al. | |
| 2006/0097025 A1 | 5/2006 | Milliman et al. | |
| 2006/0273135 A1 | 12/2006 | Beetel | |
| 2006/0278680 A1 * | 12/2006 | Viola | A61B 17/07207 227/176.1 |

FOREIGN PATENT DOCUMENTS

| | | |
|---|---|---|
| FR | 2866556 A1 | 8/2005 |
| WO | 03/020139 A2 | 3/2003 |
| WO | 03/090630 A3 | 4/2004 |

OTHER PUBLICATIONS

European Search Report for corresponding European Patent Application EP07002326 dated Jul. 23, 2007 (4 pages).
Canadian Office Action dated Apr. 10, 2015, issued in Canadian Appln. No. 2,852,547.
Canadian Office Action dated Feb. 5, 2016 issued in Canadian Application No. 2,852,547.

* cited by examiner

METHOD AND SYSTEM TO DETERMINE AN OPTIMAL TISSUE COMPRESSION TIME TO IMPLANT A SURGICAL ELEMENT

CROSS REFERENCE TO RELATED PATENT APPLICATIONS

This application is a continuation of U.S. patent application Ser. No. 14/446,907, filed on Jul. 30, 2014, which is a divisional of U.S. patent application Ser. No. 14/016,545, U.S. Pat. No. 8,900,164, filed on Sep. 3, 2013, which is a divisional of U.S. patent application Ser. No. 13/285,272, now U.S. Pat. No. 8,551,025, filed Oct. 31, 2011, which is a divisional of U.S. patent application Ser. No. 11/409,154 ("the '154 application"), now U.S. Pat. No. 8,062,236, filed Apr. 21, 2006, which claims the benefit of, and priority to, U.S. Provisional Patent Application Ser. Nos. 60/764,449 and 60/764,451, filed on Feb. 2, 2006. The entire contents of each of the above applications are hereby incorporated herein by reference. U.S. patent application Ser. No. 11/408,492 to Michael A. Soltz, entitled "Mechanically Tuned Buttress Material to Assist with Proper Formation of Surgical Element in Diseased Tissue," filed contemporaneously with the '154 patent application and published as U.S. 2007/0179528 is also incorporated herein by reference.

BACKGROUND

1. Technical Field

The present disclosure is directed to surgical stapling devices and sutures and, in particular, to methods and devices for providing an optimal amount of compression to the tissue for an optimal formation of the staples and sutures.

2. Description of the Related Art

Anastomosis is the surgical joining of separate hollow organ sections. Typically, an anastomotic procedure is performed during surgery in which a diseased or defective section of hollow tissue is removed. The anastomotic procedure joins or connects the remaining end tissue sections after the diseased tissue is removed. Depending on the desired anastomosis procedure, the end sections may be joined by either circular, end-to-end or side-to-side organ reconstruction methods.

In a known circular anastomotic procedure, a stapling device joins two ends of an organ section together. The stapling device can drive a circular array of staples through the end of each organ section. The device can simultaneously core any tissue interior of the driven circular array of staples to free a tubular passage. Many examples for performing circular anastomosis of hollow organs are described in U.S. Pat. Nos. 6,959,851, 6,053,390, 5,588,579, 5,119,983, 5,005,749, 4,646,745, 4,576,167, and 4,473,077, which are incorporated by reference herein in their entirety.

Typically, these devices include an elongated shaft having a handle portion at a proximal end thereof to effect actuation of the device. The device also has a staple holding component disposed at a distal end thereof. An anvil assembly including an anvil rod with an attached anvil head is mounted to the distal end of the device. The anvil is adjacent a staple holding component. Opposed end portions of tissue of the hollow organ(s) to be stapled are clamped between the anvil head and the staple holding component. The clamped tissue is stapled by driving one or more staples having a predetermined size from the staple holding component. In this manner, the ends of the staples pass through the tissue and are deformed by the anvil head. An annular knife is advanced to core tissue within the hollow organ. In this manner, the knife clears a tubular passage within the organ.

Surgical stapling devices for performing circular anastomosis have also been used to treat internal hemorrhoids in the rectum. During the use of a circular stapling device for hemorrhoid treatment, the anvil head and the staple holding component of the surgical stapling device are inserted through the anus and into the rectum with the anvil head and the staple holding component in an open or un-approximated position. Thereafter, a suture is used to pull the internal hemorrhoidal tissue and/or mucosal tissue towards the anvil rod. Next, the anvil head and the staple holding component are approximated to clamp the hemorrhoidal tissue and/or mucosal tissue between the anvil head and the staple holding component. The stapling device is fired to remove the hemorrhoidal tissue and/or mucosal tissue and staple the cut tissue. Sutures are also known in the art to connect or join tissue.

Although the use of circular anastomosis staplers for hemorrhoid treatment has many benefits, often a surgeon will encounter one or more different types of tissue in the body for which to apply a surgical element such as a staple. Some other tissue types include cardiac tissue, gastrointestinal tissue, and pulmonary tissue. In these different types of tissues, there may be a number of different other types of classes of such tissue, such as ischemic tissue, or diseased tissue, thick tissue, tissue treated with medicines or compounds, diabetic tissue, as well as numerous others.

Of utmost concern to surgeons is to ensure proper formation of the respective surgical element (such as the array of staples) into such tissue. It has been observed that with certain types of tissue such as ischemic tissue, or diabetic tissue an improved surgical outcome may occur after an amount of compression is applied to the tissue for an optimal time period.

However, further compression for a time period (after an optimal time period) is not favored. However, in the surgical environment, it is difficult to visually or audibly appreciate the optimal amount of compression that should be applied to the various tissue types, and also it is difficult to visually or audibly appreciate the optimal time period for tissue compression.

Accordingly, a continuing need exists in the art for a device for the treatment of tissue which can quickly and easily compress tissue prior to applying a surgical element in the tissue for an optimal time period. It is a further need in the art for a device that can compress tissue and then communicate an indication to the surgeon that a threshold has been reached and that the surgical element should be applied to the tissue for proper formation of the surgical element such as a staple or a suture.

SUMMARY

According to an aspect of the present disclosure, there is provided a method for determining an optimal compression of tissue to apply a surgical element. The method has the step of applying a load to the tissue. The method also has the step of determining a reactive load applied by the tissue in response to the load. The method further has the step of determining the reactive load per unit time for a predetermined time period and determining a slope of the reactive load per unit time. The method further has the steps of evaluating the slope relative to a predetermined threshold, and signaling when the slope exceeds the predetermined threshold.

According to another aspect of the present disclosure, there is provided an apparatus for determining an optimal amount of tissue compression prior to the insertion of a surgical element into the tissue. The apparatus has a measuring device configured to detect a tissue parameter upon the compression of the tissue. When the measuring device reaches a threshold after the tissue is compressed for a predetermined time period, an indicator indicates to the surgeon the event of the threshold and that the surgical element is ready to be inserted to the compressed tissue. The threshold is indicative of the surgical element being properly formed in the tissue at the indicated time period. When the compression is lifted after the threshold, the tissue with the surgical element returns to a substantially an uncompressed state without necrosis.

According to yet another aspect of the present disclosure there is provided a method for determining an optimal compression of tissue to apply a surgical element. The method has the steps of measuring an initial tissue thickness and applying a load to the tissue. The method also has the steps of determining a physiological event of the tissue in response to the load applied and measuring the thickness at the event. The method also modulates a surgical instrument in response to the thickness at the event.

According to another aspect of the present disclosure there is provided a device for determining an optimal amount of compression of tissue to apply a surgical element. The device has a body with a handle assembly connected to a shaft, and a load cell assembly with a load cell. The device also has a movable platen and a stationary platen connected to the shaft. The movable platen compresses the tissue between the stationary platen to apply a load to the tissue. The load cell is disposed in contact with the movable platen to determine a reactive load applied by the tissue in response to the load. The device also has a controller configured to determine the reactive load per unit time for a predetermined time period.

According to a further aspect of the present disclosure, there is provided an apparatus to determine an optimal amount of strain on tissue to apply a surgical element. The apparatus has a first caliper arm and a second caliper arm and a body connected to the first caliper arm and the second caliper arm. The distance between the first caliper arm and the second caliper arm is measured as a gap. The first caliper arm is movable with respect to the second caliper arm and is adapted to move in a direction toward to the second caliper arm to measure an initial tissue thickness in the gap. The first caliper arm and the second caliper arm can further move toward one another to apply a load to the tissue to compress the tissue to a predetermined tissue thickness. The predetermined tissue thickness corresponds to the optimal amount of strain on the tissue suitable to apply the surgical element into tissue.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
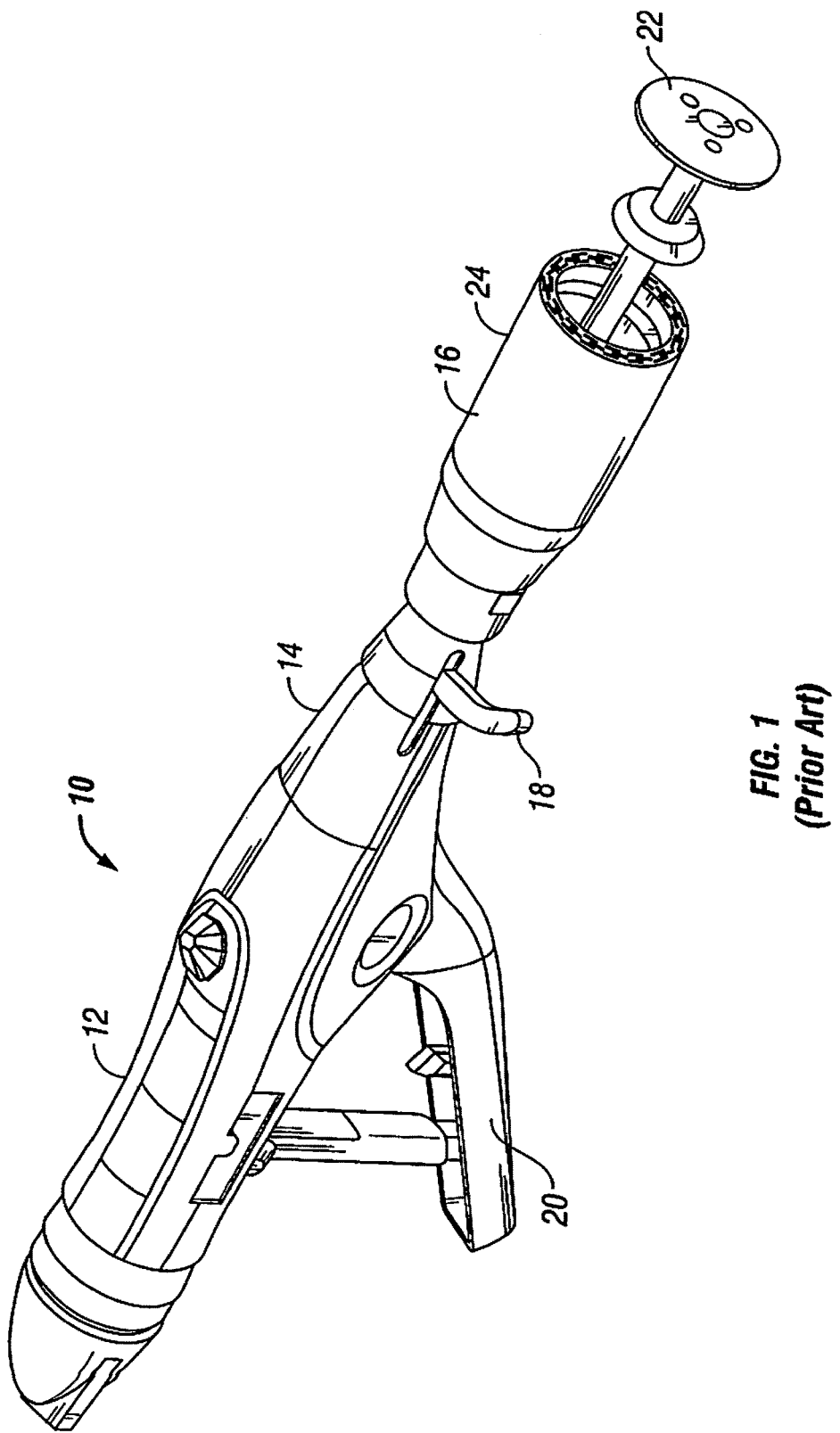
FIG. 1 is a perspective view of a device for implanting a surgical element into tissue.

Embodiments of the presently disclosed method, apparatus and system will be described herein below with reference to the accompanying drawing figures wherein like reference numerals identify similar or identical elements. In the following description, well-known functions or constructions are not described in detail to avoid obscuring the disclosure in unnecessary detail.

Referring to FIG. 1, there is shown a device for applying a surgical element to tissue. This device is described in U.S. Pat. No. 6,959,851. In one embodiment, the device is a stapling device 10 having a proximal handle assembly 12, a central body portion 14 and a distal head portion 16.

The proximal handle assembly 12 has a rotatable approximation knob 18 and a firing trigger 20. The approximation knob 18 is operable to move anvil 22 in relation to shell assembly 24 of head portion 16 between spaced and approximated positions and firing trigger 20 is operable to eject surgical elements (fasteners) from shell assembly 24 and advance a knife blade through shell assembly 24 to cut tissue.

In gastrointestinal surgery, the goal of the surgery is to provide for a hemostatic leak free joint by mechanically compressing the tissue. However, various tissue specific considerations may exist that can effect blood perfusion to the anastomotic wound. Some considerations include poor blood supply, ischemia, diabetes, tissue thickness, and poor fluid flow through the tissue.

In one aspect the present disclosure provides for a method of improved staple formation to give surgeons more flexibility in the surgical environment. The improved staple formation provides that two or more desired sections of tissue can be joined to achieve acceptable and proper staple formation and whereas the two joined tissue sections will be permanently joined and heal without any leakage.

Figure 2:
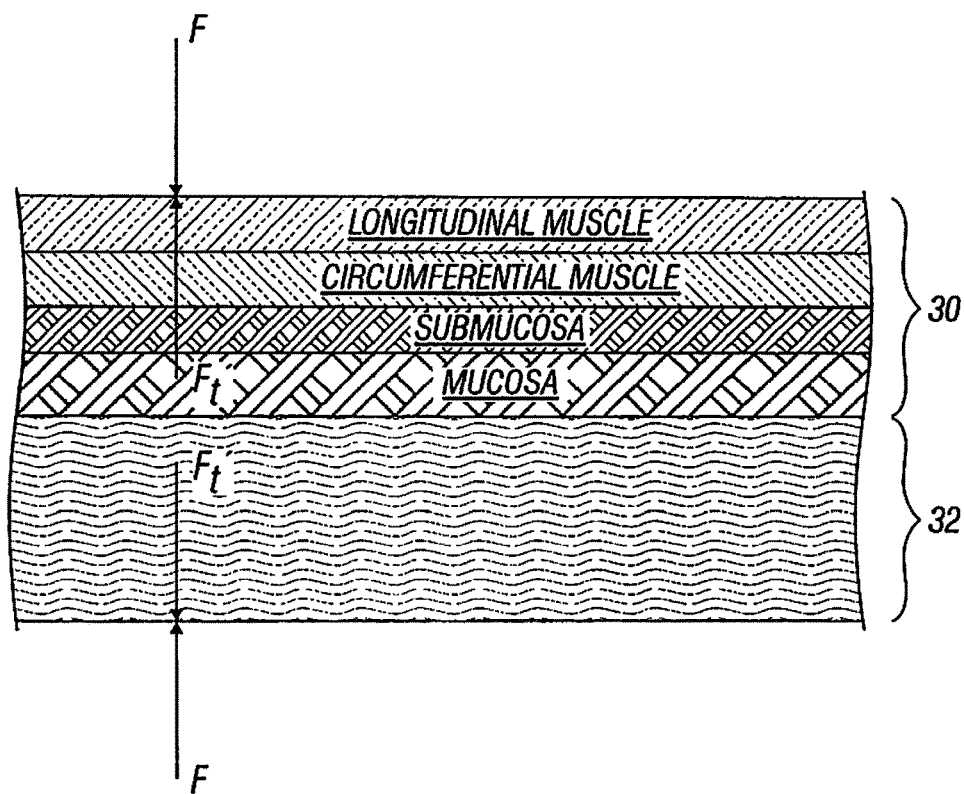
FIG. 2 is a schematic illustration of a first tissue section being compressed to a second tissue section according to an embodiment of the present disclosure with the tissue responding by imparting a reaction force in response to the compression.

FIG. 2 shows a first discrete tissue section 30, and a second discrete tissue section 32. Each has various layers such as longitudinal muscle, circumferential muscle, sub mucosa, and mucosa. The present method provides for determining an optimal amount of compression to the two tissue sections 30, 32, prior to introducing any surgical element in order to pre-treat the tissue sections. Thereafter, only after the tissue sections 30, 32 have been pretreated with the optimal amount of compression, are the two tissue sections 30, 32 ready to be joined by the surgical element.

In one example, the first tissue section 30 will be compressed at the same time as the second tissue section 32. In another example, each of the tissue sections 30, 32 may be individually compressed with the optimal amount of compression. In still another embodiment, tissue sections (not shown) may be compressed in a radial manner with the optimal amount of compression, and then joined with an array of surgical elements. Various configurations are possible and within the present disclosure.

According to another aspect of the present disclosure, the insertion of a surgical element such as a staple for proper staple formation can be thought of as a stress relaxation experiment. Stress relaxation with viscoelastic materials is achieved when a force from the tissue does not change per unit time, or changes negligibly over time.

Figure 5:
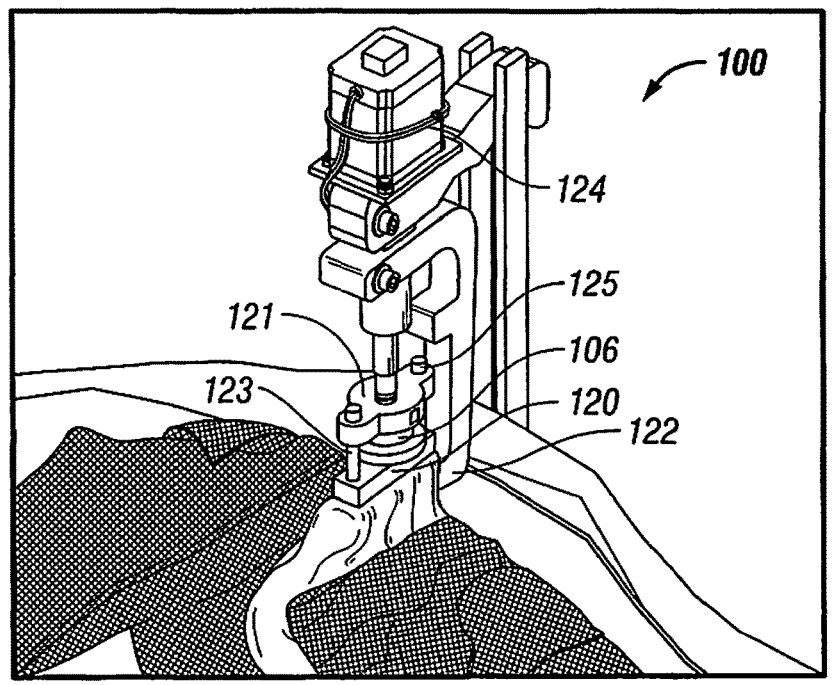
FIGS. 5 and 6 are perspective views of the system with the load cell and movable platen compressing the tissue with FIG. 5 showing a mechanical loading of the tissue and FIG. 6 showing tissue clamped between the jaws.
Figure 6:
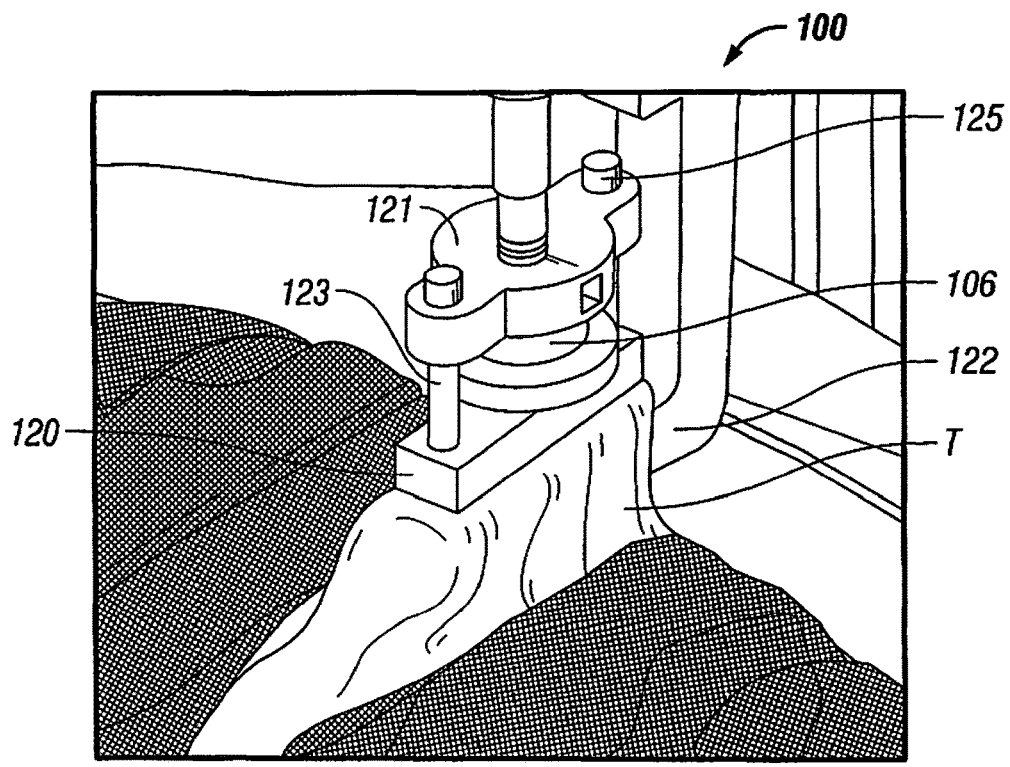

In this aspect, the tissue is loaded between a first platen 120 and a second platen 122 as shown in FIGS. 5 and 6 which will be discussed in detail hereafter. The moveable platen 120 is actuated to compress the tissue to a desired final thickness. As shown in FIG. 2, during a time period of the compression, the tissue resists the deformation by the tissue exerting a reaction force Ft in response to the compression force on the tissue F.

In viscoelastic materials, faster compression creates greater reaction forces. The model of stress relaxation is based on Fung's Quasi-Linear Viscoelasticity Theory. For a tissue specimen of biological tissue subjected to compressive deformation, if a step increase in compression is made on the tissue specimen, the stress developed will be a function of time (t), and the strain ($\varepsilon$).

The history of the stress called the relaxation function, $K(\varepsilon, t)$ will be of the form of:

$$K(\varepsilon,t)=G(t)T^e(\varepsilon) \quad \text{Equation (1)}$$

Where $G(t)$ is the reduced relaxation function, and represents the normalized function of time, and $T(\varepsilon)$ is the elastic response of the tissue. It is assumed that the stress response to a change in strain $d\varepsilon(t)$, superimposed on a specimen in a state of strain $\varepsilon$ at time t where:

$$G(t-\tau)\frac{\partial T^e[\varepsilon(\tau)]}{\partial \varepsilon}\partial \varepsilon(\tau) \quad \text{Equation (2)}$$

The total stress T(t), is given by:

$$T(t) = \int_{-\infty}^{t} G(t-\tau)\frac{\partial T^e[\varepsilon(\tau)]}{\partial \varepsilon}\frac{\partial \varepsilon(\tau)}{\partial \tau}d\tau \quad \text{Equation (3)}$$

Therefore, the total stress at time t is the sum of contributions of all of the past changes, with the same reduced relaxation function.

When the force is applied at the tissue at time t=0, and $\sigma_v = \varepsilon_v = 0$ for t<0 Then Equation 3 reduces to:

$$T(t) = T^e(0^+)G(t) + \int_0^t G(t-\tau)\frac{\partial T^e[\varepsilon(\tau)]}{\partial \tau}d\tau \quad \text{Equation (4)}$$

And if, $\partial T^e/\partial t$, $\partial G/\partial t$ are continuous, then the above equation is equivalent to:

$$T(t) = G(0)T^e(t) + \int_0^t T^e(t-\tau)\frac{\partial G}{\partial t}d\tau \quad \text{Equation (5, 6)}$$

$$= \frac{\partial}{\partial t}\int_0^t T^e(t-\tau)G(\tau)d\tau$$

In the Laplace Domain, the total stress is given by:

$$\overline{T}(s) = L\{T(t)\} = \int_0^\infty T(t)e^{-st}dt \quad \text{Equation (7)}$$

Applying this transformation to T(t), in Equation 6, the total stress is:

$$\overline{T}(s) = L\left\{\frac{\partial}{\partial t}\int_0^t T^e(t-\tau)G(\tau)d\tau\right\} = L\left\{\frac{\partial}{\partial t}[T^e(t)*G(t)]\right\} \quad \text{Equation (8)}$$

For a general function f(t), the transformation of the first derivative df/dt is calculated as $$L\{df/dt\}=sF(s)-f(0^-)$$

Similarly, the transformation of the convolution in Equation 8 is:

$$\overline{T}(s)=s\overline{T}^e(s)\overline{G}(s)-T^e(0^-)G(0^-) \quad \text{Equation (9)}$$

The reduced relaxation function G(t), has been readily used to describe the behavior of biological tissues and is defined as:

$$G(t) = \frac{1 + c\left[E_t\left(\frac{t}{\tau_2}\right) - E_t\left(\frac{t}{\tau_1}\right)\right]}{1 + cln\left(\frac{\tau_2}{\tau_1}\right)}$$ Equation (10)

Where E1(z) is the exponential integral function defined by the equation:

$$E_t(z) = \int_z^\infty \frac{e^{-1}}{t} dt, (|\arg z| < \pi)$$

Therefore G(s) is given by:

$$\overline{G}(s) = \frac{G(\infty)}{s}\left\{1 + cln\left[\frac{(1+s\tau_2)}{(1+s\tau_1)}\right]\right\}$$ Equation (11)

and, $$G(\infty) = \left[1 + cln\left(\frac{\tau_2}{\tau_1}\right)\right]^{-1}$$ Equation (11)

In the current analysis, it is assumed that the elastic response is a linear function of strain, i.e.:

$$T^e(\varepsilon(t)) = As(t)$$

Although biological tissues generally posses non-linear stress-strain dependence, the current linear formation is sufficient to curve fit the response or force imposed by the tissue tested at one level of compression. This, from equation 9 listed above, it is observed that the total stress in the Laplace Domain is:

$$\overline{T}(S) = AL\{\varepsilon(t)\}G(\infty)\left\{1 + cln\left[\frac{(1+s\tau_2)}{(1+s\tau_1)}\right]\right\}$$ Equation (12)

Where A is the elastic stiffness of the tissue, c represents the relaxation index, τ1 is the short relaxation constant, and τ2 is the long relaxation constant.

In Equation 12, L(ε(t)) represents the Laplace Transform of the applied strain function. The total stress T(t) can be determined numerically by calculating the inverse Laplace Transform of T(s).

Figure 3:
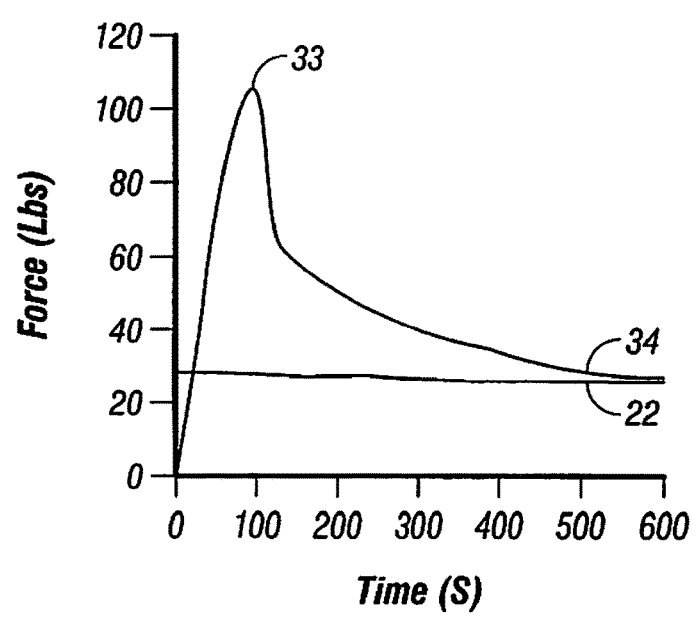
FIG. 3 is a plot of a predicted force versus time for a rapid loading compression of gastrointestinal tissue for a 1.5 mm gap distance with the plot showing the equilibrium state of the viscoelastic tissue.

Referring now to FIG. 3, there is shown the predicted force of the tissue in response to the compression of the movable platen 120 shown in FIGS. 5 and 6 for rapid loading compression of a surgical element to tissue. In this embodiment, the tissue is gastrointestinal tissue; however, the present analysis can be extended to other tissue types. In the embodiment shown in FIG. 3, the tissue is compressed to about 1.5 mm to have an equivalent instrument gap distance as measured between the anvil and the cartridge of a surgical stapler.

The model described above is an algorithm to determine the material properties of tissue including the Viscoelastic Index (c), the short time constant (τ1), and the long time constant (τ2) as well as the equilibrium modulus of the tissue (A). To apply this module to stapling, the reaction force Ft that is shown in FIG. 2 is determined. By curve fitting this force Ft response, the material properties of the specific tissue can be extracted for this individual patient, and the optimal amount of compression and time of compression for the individual patient can be determined.

Figure 3A:
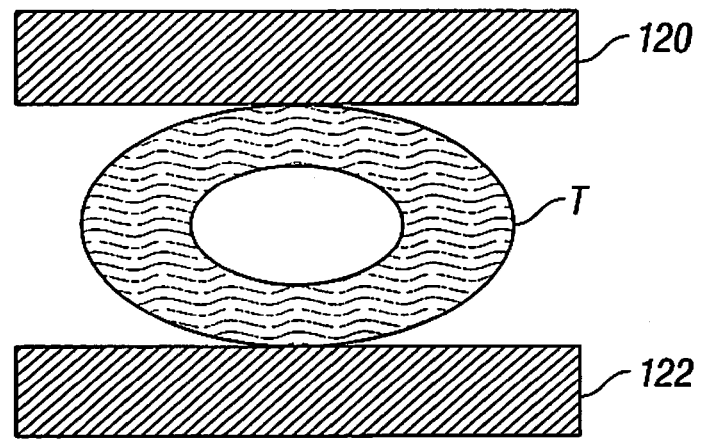
FIG. 3A is a view of tissue being between a moveable platen and a stationary platen showing the tissue having an initial tissue thickness.
Figure 3B:
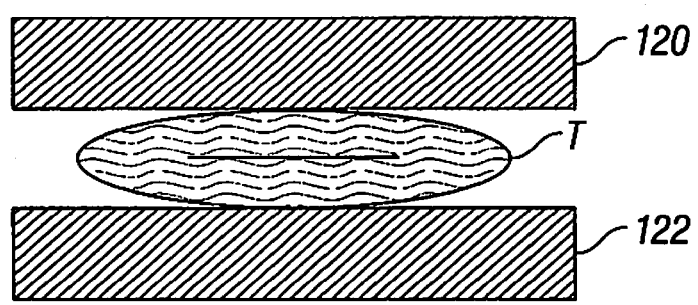
FIG. 3B is a view of tissue being compressed between a moveable platen and a stationary platen showing the tissue having an final gap thickness.

The model can also be used to predict behavior of the tissue 30, 32 when stapled under various conditions such as rapid or slow compression as shown in FIG. 3. As is understood in FIGS. 3A and 3B, the tissue disposed between a first platen 120 and a second platen 122 with have an initial tissue thickness as shown in FIG. 3A, and then will be compressed to a final gap thickness as shown in FIG. 3B; however the tissue will impart a reaction force as discussed herein.

Referring now to FIG. 3, as can be seen the x-axis is time in seconds. The y-axis shows the reaction force of the tissue in pounds in response to the compression. The y-axis can alternatively be measure in other increments such as Newtons.

As can be understood, the tissue exerts a peak force 33 immediately within 100 seconds of about 80 pounds. This peak force 33 is not the ideal time for this specific tissue sample to apply the desired surgical element based on the amount of compression that is exerted on the tissue. Thereafter, as time elapses to 200 seconds, the reaction force is about 40 pounds. Thereafter, as further time elapses to 300 seconds the reaction force is about 30 pounds. Thereafter, as further time elapses to 400 seconds the reaction force is about 22 pounds. Thereafter, as further time elapses to 500 seconds the reaction force is about 20 pounds. Further, as more time elapses to 600 seconds the reaction force is still and remains at about 20 pounds.

Thus, it is observed from FIG. 3, that the proper time to apply the surgical element is at the equilibrium state 34 or when the slope of the curve (of the reaction force over time) approaches a predetermined threshold or when the slope has a negligible change per unit time as shown by reference numeral 34. The reaction force exerted by the tissue at this point is called the equilibrium force 34. In one embodiment, the slope may arrive at zero. At another embodiment, the slope may be markedly less relative to the slope at 100 seconds from when compression is initially applied to tissue. In another embodiment, the slope may simply arrive and be maintained at a predetermined value or threshold. Various configurations are possible and within the scope of the present disclosure.

Figure 3C:
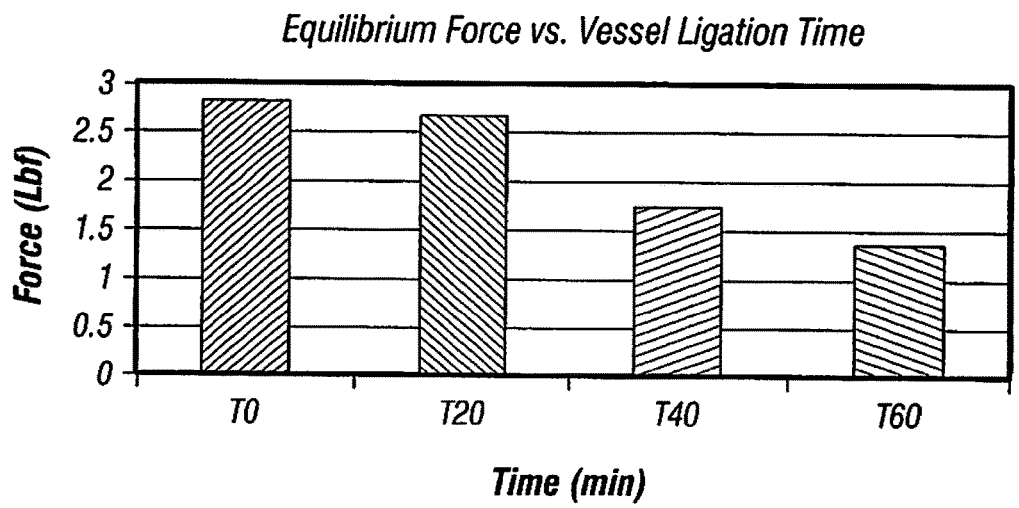
FIG. 3C is a plot of the equilibrium force of the tissue versus the time.

Referring now to the plot shown as FIG. 3C, there is shown a plot of the equilibrium force of the tissue over time. In the plot shown as FIG. 3C, it is understood that the equilibrium force imparted by the tissue decreases over one hour as shown in T6. In this plot, tissue was compressed for ten minutes and then allowed to rest without compression for ten minutes in a repeated cycle for one hour. The tissue was transected and cut from all blood supply and fluid supply for the experiment. Due to the compression over the time period the stiffness of the tissue decreased as shown in FIG. 3C. Over the elapsed time the tissue was perceived to be softer.

Figure 3D:
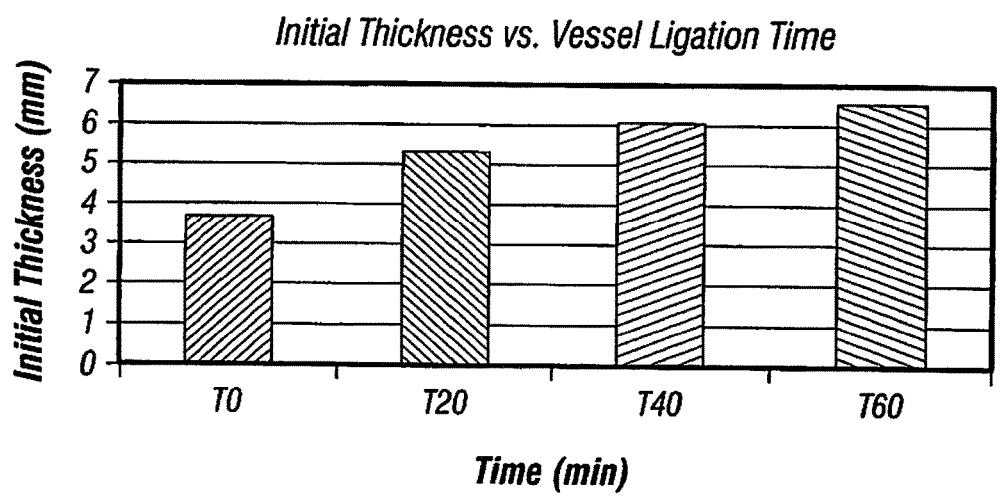
FIG. 3D is a plot of a variation of the tissue thickness versus time.

Referring now to the plot shown as FIG. 3D, there is shown a plot of the thickness of the tissue over time. In the plot shown as FIG. 3D, it is understood that the thickness of the tissue shown in millimeters increases over the shown time period by about nearly 75 percent. It was observed that due to the compression, tissue thickness increases due possibly to the spasmodic effect of the tissue to encourage blood or fluid to return to and traverses through the tissue.

Figure 3E:
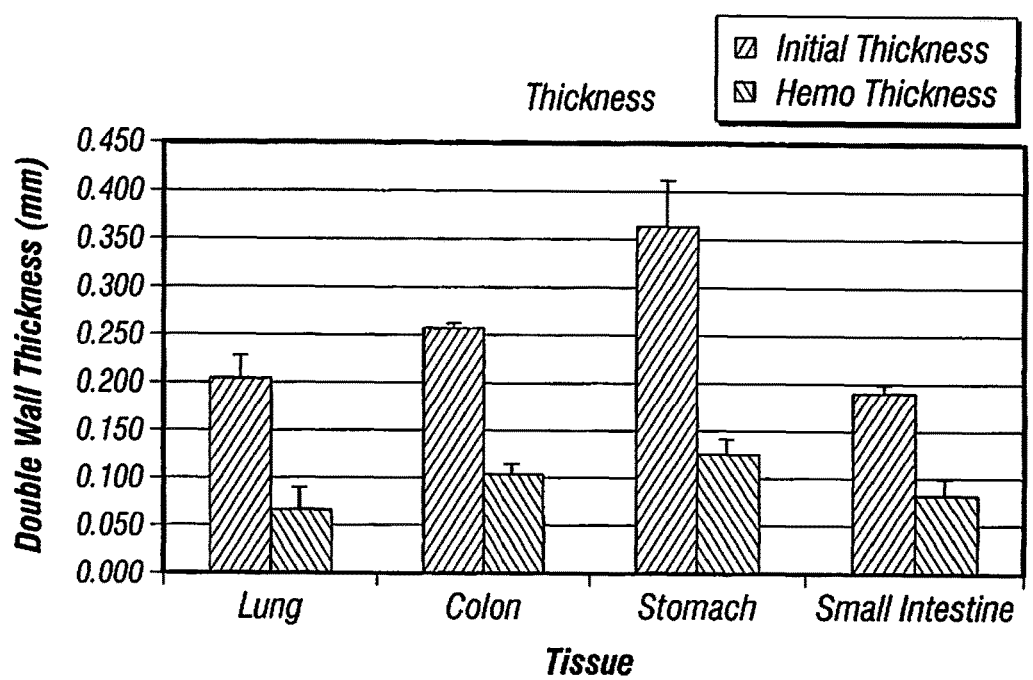
FIG. 3E is a plot of the initial and hemostasis thickness for various tissues.

Referring now to the plot shown as FIG. 3E, there is shown a plot of the initial thickness of the tissue over time, and the thickness of the tissue where hemostasis is observed to occur. In the plot shown as FIG. 3E, it is understood that for different tissue types such as lung tissue, colon tissue, stomach tissue, and small intestinal tissue, and amount of compression to a determined hemostasis thickness of tissue can also collapse the blood vessels to assist with hemostasis, and will be discussed in detail below.

Figure 4:
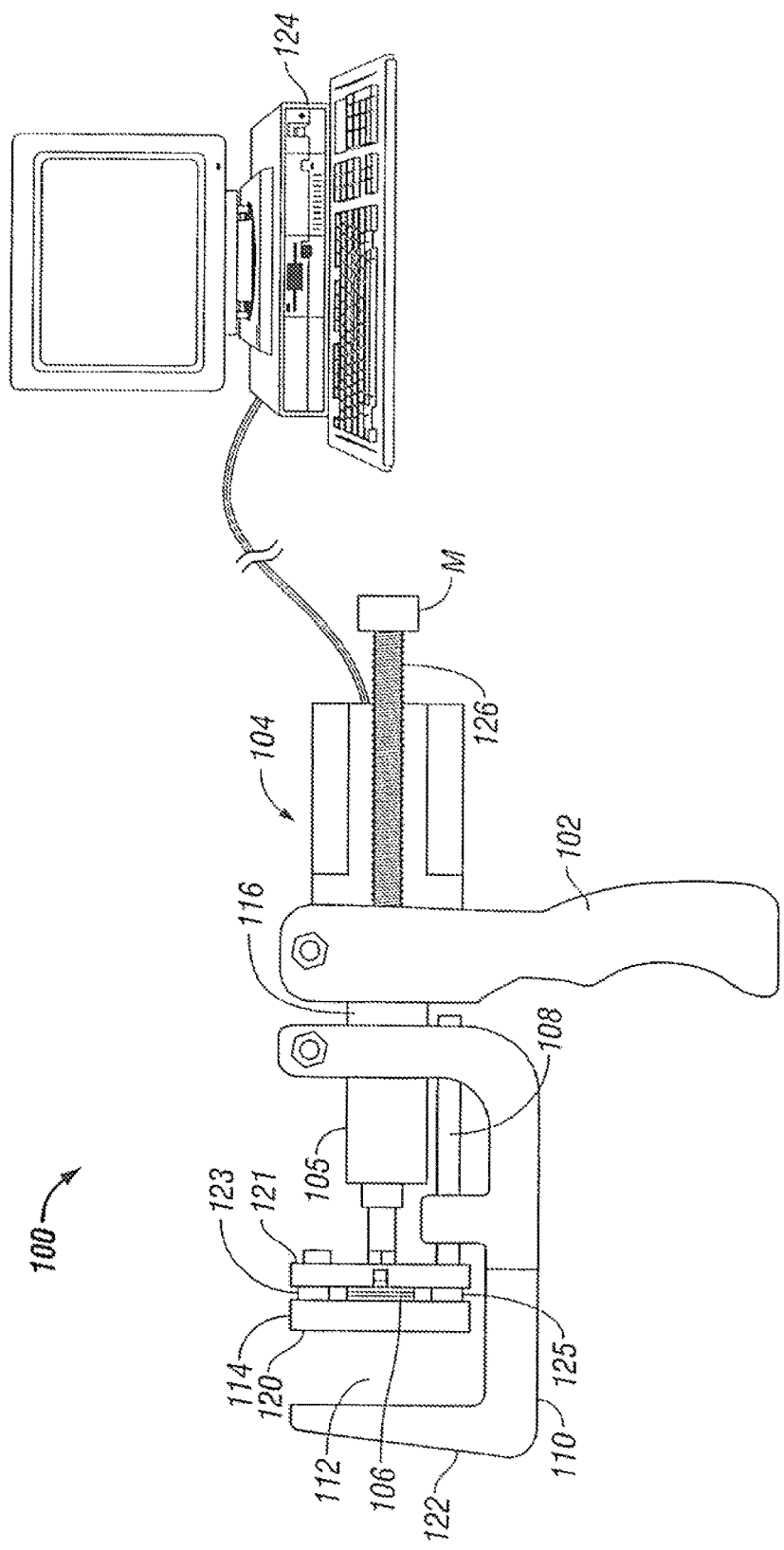
FIG. 4 is an illustration of a system for determining an optimal compression time with the system having a movable platen, a stationary platen and a load cell according to the present disclosure.

Referring now to FIG. 4, there is shown the device 100 for measuring the mechanical properties of the tissue. The device 100 has a handle assembly 102, and a shaft assembly 104. The shaft assembly 104 is connected to the handle assembly 102. The shaft assembly 104 also has a load cell assembly 106. The load cell assembly 106 includes a transducer which converts a force into a measurable electrical output. The load cell assembly 106 may be placed on various locations of the device 10 and is shown between the movable platen 120 and a support plate 121 for illustration purposes only. The load cell assembly 106 may be placed in other locations such as those disclosed in United States Published Patent Application No. US 2005/0131390 to Heinrich, et al., which is herein incorporated by reference in its entirety. In one alternative embodiment, the device 100 can be formed with a load cell 106 placed in or against the stationary platen 122.

In one embodiment, the load cell assembly 106 includes a strain gage based load cell. In another embodiment, the load cell assembly 106 may include a mechanical load cell assembly such as a hydraulic load cell, or a pneumatic load cell. Still alternatively, the load cell assembly 106 may be a strain gauge load cell such as a bending beam load cell, a shear beam load cell, a canister load cell, a ring and so called "pancake load cell", a button and washer load cell, or a helical or fiber optic load cell. Various configurations of the load cell assembly 106 are possible and within the present disclosure, and it is appreciated that the load cell assembly 106 may be any device in order to determine the force imparted by the tissue in response to the compressive load.

The device 100 has a guide pin 108 and a rigid frame 110. Advantageously, the device 100 has a tissue gap insertion portion 112 where several different tissue types may be easily inserted or placed between without regard to the thickness of the tissue or the tissue type. In this aspect, the device 100 has a clamp bar 114 to clamp on the tissue. The device 100 also has a load cell assembly 106. The load cell assembly 106 is advantageously disposed between a movable platen 120 and a support plate 121. The support plate 121 is connected to the moveable platen 120 by a first guide bar 123 and a second guide bar 125 to ensure linear movement of the load cell as the moveable platen 120 is advanced distally toward a stationary platen 122. Guide pin 108 connects with the second guide bar 125 and connects the plate 121 with the movable platen 120.

The pusher 116 is adapted to place a know deformation on to the tissue by the moveable platen 122. The pusher 116 may be a piston or similar structure and connected to a motor, or alternatively may be manually operated. The moveable platen 122 contacts the load cell 106 that is disposed between the plate 121 and the moveable platen 122. The load cell 106 in contact with the moveable platen 122 simultaneously measures the reaction force of the tissue. The tissue has an initial thickness that is measured with a caliper or similar device and recorded. The load cell assembly 106 is preferably disposed between the plate 121 and the movable platen 120. The moveable platen 120 and the stationary platen 122 that are separated from one another by a selectable gap in the tissue gap insertion portion 112. The movable platen 120 is illustratively operatively connected to a motor M by a lead screw assembly 126. Although, illustrated schematically, the motor M may be separate from the device 100 or compact enough to be placed in the shaft assembly 104.

Figure 4A:
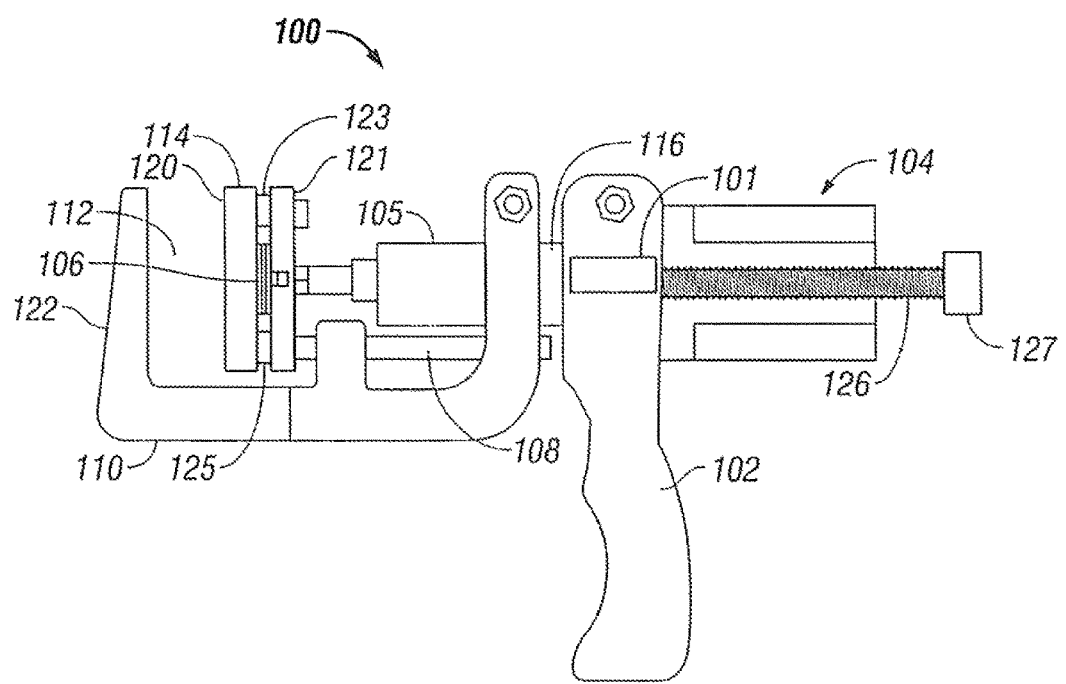
FIG. 4A is an illustration of a manual system for determining an optimal compression time with the system having a movable platen, a stationary platen, a load cell, and a display screen.

Another embodiment of the present disclosure is shown in FIG. 4A. In this embodiment, the device 100 is a more compact device than the embodiment of the FIG. 4, and instead of a motorized operation the device 100, the device 100 for measuring the mechanical properties of the tissue may be manually operated. The device 100 may not be connected to any external devices as in FIG. 4, but instead be suited for more dynamic working conditions. Again, the device 100 has a handle assembly 102, and a shaft assembly 104. The shaft assembly 104 is connected to the handle assembly 102 and also has a load cell assembly 106 being disposed between the plate 121 and the moveable platen 120.

The load cell assembly 106 includes a transducer which converts a force into a measurable electrical output. The load cell assembly 106 also has circuitry that is adapted to convert a format of the output to display the output on a screen 101. The pusher 116 is adapted so the moveable platen 120 places a know deformation on to the tissue. The moveable platen 120 will further contact the load cell assembly 106 to measure the reaction force. The tissue has an initial thickness that is measured with a caliper or similar device and recorded. The load cell assembly 106 contacts the movable platen 120 that is separated from the stationary platen 122 by the selectable gap in the tissue gap insertion portion 112. In this embodiment, the movable platen 120 is connected to the drive screw 126, and the surgeon can manually advance the movable platen 120 distally in a direction toward the stationary platen 122 using actuator 127. Once the displayed force on the screen 101 changes negligibly per unit time, or alternatively stops changing per unit time the surgeon will know that the tissue has reached the equilibrium state, and it is the correct time to implant the surgical element. The device 100 may optionally not display the force on the screen 101 and instead be formed with an alarm that signals the surgeon that the tissue has reached the equilibrium state. Various configuration and possible and are within the present disclosure.

Referring now to FIGS. 5, and 6, there is shown the device 100 of FIG. 4 in operation. The initial thickness is measured when there is little or no load on the tissue T. Thereafter, the load cell assembly 106 has the movable platen 120 moving toward the stationary platen 122 to compress the tissue T (as shown in FIG. 6) to apply a predetermined load on the tissue. The reaction force from the tissue and the displacement of the tissue are recorded by the load cell assembly 106 until the desired final thickness is reached. Once reached, and the tissue T has reached substantially an equilibrium state, the device 100 will signal an alarm that the optimal compression time has been reached, and that a surgical element may be introduced through the tissue. The equilibrium state is defined as the zero slope of the curve as shown in FIG. 3, or a state that the tissue enters when the tissue reactive force per unit time is about zero or changes negligibly per unit time.

FIG. 6 shows the tissue T disposed between the movable platen 120 and the stationary platen 122. Given the viscoelastic properties of the tissue T, it is understood that it is desirable to compress the tissue until the slope of the tissue reaction force per unit time reaches zero or a negligible amount after being compressed for a period of time. The load cell assembly 106 communicates electronic signals from the load cell assembly to a controller 124 shown schematically in FIG. 4.

The controller 124 of the device includes programmable instructions and will monitor one or more parameters of the procedure. In one embodiment, the controller 124 may have a control system may include one or more digital signal processors and a control module executable on the processor(s). The digital processor(s) and/or control module may include one or more digital signal processors (DSP) and associated circuitry. The controller 124 may further include circuitry including analog, digital and/or logic devices (not explicitly shown). The DSPs may be upgradeable using flash ROM as is known in the art. Upgrades for the DSPs may be stored on computer readable media such as compact flash media, magnetic disks, optical disks, magnetic tape, or other suitable media so as to be compact. Furthermore, the controller 124 may reside at least partially on the remote processor. The DSPs could be replaced by any system capable of mathematic operations. In one such embodiment, the control system 124 may be a field programmable gate array.

In one embodiment, the controller 124 measures the reaction force of the tissue with the load cell assembly 106 per unit time. It should be appreciated that after a point 34 as illustrated on the plot of FIG. 3, the reaction force does not change with time or changes only a predetermined amount over time. The device 100 has the load cell assembly 106 that detects the reaction force at a first time interval, and then sequentially to another or later second time interval. The device 100 will further measure the force at a number of increments over a period of time. The controller 124 will then determine the slope of the curve of the reaction force over the period of time. The controller 124 will then compare the slope of the curve to a threshold value. If the controller 124 determines that the slope has exceeded the threshold value, the controller 124 will control an audible alarm (not shown) to signal to the surgeon that the tissue has reached the optimal compression value, and that any further compression is unnecessary and that the surgical element is ready to be introduced into the tissue for joining the tissue sections together. In another embodiment, of the present disclosure, the device 100 may have a strain gauge instead of the load cell 106 to measure the reaction force of the load on the tissue. In still another embodiment, the device 100 may have a pressure gauge, instead of the load cell. Various configurations are possible and within the scope of the present disclosure.

In another embodiment of the present disclosure, the controller 124 may receive other parameters instead of deformation in order to calculate the slope and compare the slope to the threshold. The controller 124 in one embodiment may measure distance, and/or velocity of the moveable platen 120. The controller 124 may measure, the distance relative to a predetermined distance threshold, of for example eighty percent compression of the initial thickness without any load being applied. Once threshold distance is achieved, the controller 124 controls the audible alarm to signal the surgeon that the optimal amount of compression has been achieved and the surgical element should be applied to the tissue.

Figure 7:
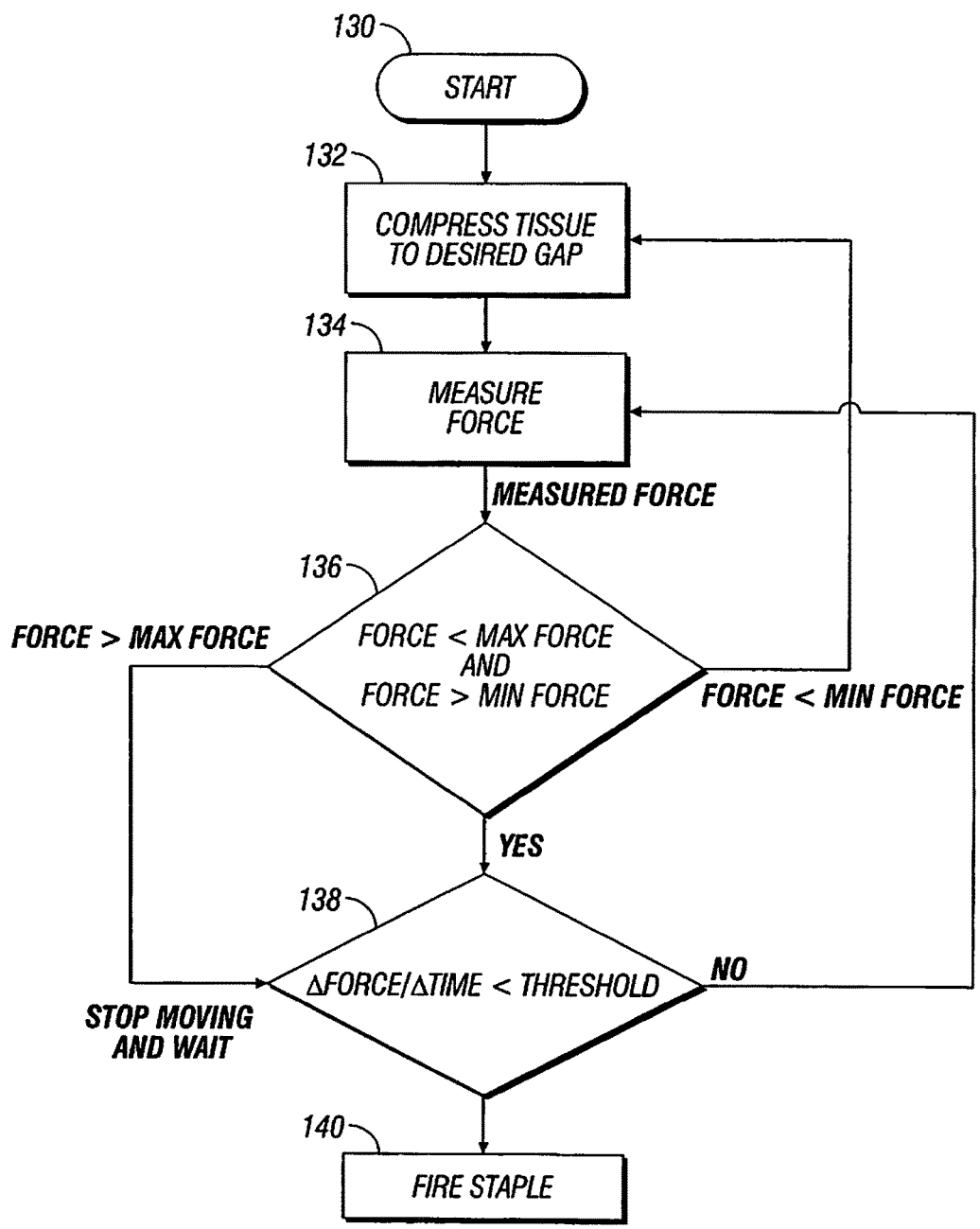
FIG. 7 shows a schematic block diagram according to a method of the present disclosure for compressing tissue to determine an optimal amount of compression and a optimal time for which to implant a surgical element into the tissue.

Referring now to FIG. 7, there is show a schematic block diagram that the controller 124 of the device 100 may use in order to determine the optimal compression time of the tissue prior to implanting a surgical element into the tissue. The method commences at step 130. At step 132, the method has the step of compressing the tissue to a desired gap. Thereafter, the method continues to step 134 and measures a reaction force of the tissue in response to the compression. Thereafter, the method may further have the step of recording the reaction force in a memory. The method then arrives at a decision block at step 136.

At decision 136, the method has the step of determining whether the reaction force is in a predetermined range. If the measured force is less than a minimum force, then the force is insufficient and the method returns to step 132 to compress the tissue to the desired gap.

At decision 136, if the measured force is greater than a maximum force at step 136, then the force may be too great and method proceeds to step 138 to stop the movable platen 120 and proceed to wait. If the measured force is greater than a minimum force at step 136, and the force is less than the maximum force, the method continues to decision step 138.

At step 138, the controller 124 will determine a slope of the change in the reaction force over the change in time to determine a parameter. At step 138, the controller 124 will evaluate the parameter with regard to a predetermined threshold. In one embodiment, the predetermined threshold will be the slope of the plot shown in FIG. 3. In this manner, when the slope is zero, or at a negligible change shown by reference numeral 34 on the plot, this indicates to the controller 124 that the tissue has reached a state that is indicative of optimal amount of compression of the viscoelastic tissue and the surgical element should be introduced into the tissue to ensure proper formation of the surgical element at step 140.

Thereafter, if the controller 124 reaches the predetermined threshold, then the method proceeds to step 140 where the device 100 may have an audible alarm, or a visual alarm to indicate that the surgeon should fire the surgical element such as a staple.

In another embodiment, if the controller 124 reaches the predetermined threshold, then the method proceeds to step 140 where the device 100 may be connected to the firing mechanism of the stapler of FIG. 1 to automatically fire the surgical element such as a staple into the tissue. If the controller 124 at step 138 does not reach the predetermined threshold, then the method proceeds back to step 134 where the device 100 may continue to apply compression on the tissue, and measure the reaction force of the tissue over time. It should be appreciated that in no instance is the tissue compressed for more than twenty minutes at this may lead to excessive compression and inadequate blood flow to the tissue. The controller 124 has program instructions to release the tissue if compressed for more than an allotted time period such as twenty minutes.

In yet another embodiment of the present disclosure, the device 100 may measure a velocity or an acceleration of the moveable platen 120. The controller 124 may measure the velocity or the change of velocity relative to a predetermined distance threshold. In one example, the controller 124 may measure a predetermined velocity of the movable platen 120 when about eighty percent compression of the initial thickness (without any load being applied) is reached. Once threshold is achieved, the controller 124 will control the audible alarm to signal the surgeon that the optimal amount of compression has been achieved and the surgical element should be applied to the tissue to join the tissue sections to one another.

In a further embodiment of the present disclosure, the movable platen 120 and the stationary platen 122 of the device 100 have a predetermined geometry that is complementary to the end effector geometry of the instrument used in the procedure. In one embodiment, where the surgical element is a surgical staple made from a biocompatible material such as titanium, the movable platen 120 and the stationary platen 122 have a compression area that is the same as the jaws of a surgical stapler.

Figure 8:
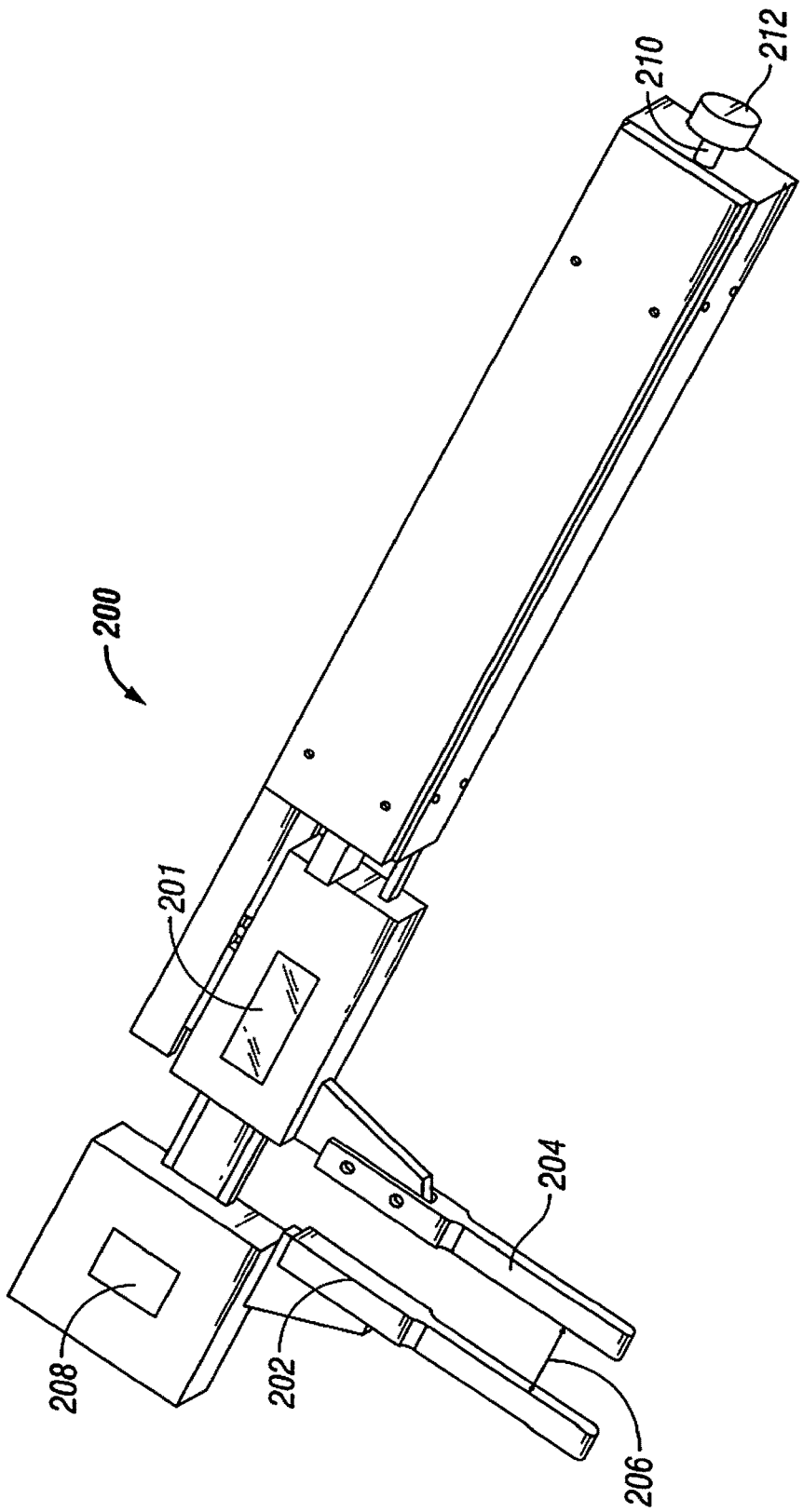
FIG. 8 is a caliper device for determining an initial tissue thickness and a hemostasis thickness of the tissue.

Referring now to FIGS. 8 through 13, there is shown another embodiment of the present disclosure. In this embodiment, the method has the steps of measuring an initial thickness of tissue. Thereafter, the tissue is compressed with a device 200 and a final thickness of tissue at a physiological response is taken. This final thickness is used to modulate one or more parameters of the surgical procedure. FIG. 8 shows a modified caliper device 200 having a first caliper arm 202 and a second caliper arm 204 defining a tissue gap 206 between the first caliper arm 202 and the second caliper arm 204. The caliper device 200 also has a sensor 208. The sensor 208 is an optical or resistive element to indicate visually, or audible that the device 200 is contacting tissue.

The caliper device 200 on an opposite end has a threaded arm 210 with an actuator 212 that is connected to the caliper arms 202, 204, and that permits the surgeon to manually rotate the actuator 212 to draw the first caliper arm 202 to the second caliper arm 204 with the tissue disposed between the first and second caliper arms 202, 204 in the gap 206. The caliper device 200 also can have an indicator or screen 201 that visually indicates the thickness of the tissue such as a manually with a dial, or digitally with a LED, or display screen. The screen 201 may be a liquid crystal digital display showing the unit of measurement. Alternatively, the screen 201 can be a conventional analog display or dial showing units of measurement in inches or millimeters. Alternatively, the caliper device 200 may be connected to an analog to digital converter to convert an analog signal to a digital signal to communicate the thickness electronically to the controller 124.

In this embodiment, it is envisioned that an optimal amount of strain on tissue is required to mechanically control bleeding and is desired to improve surgical outcomes. It should be also appreciated that a predetermined amount of strain applied to tissue is known. This predetermined amount of strain will collapse the blood vessels to promote hemostasis. However, this predetermined amount of strain to promote hemostasis varies for different types of tissue. Gastrointestinal tissue, pulmonary tissue, abdominal tissue, colonic tissue or small intestinal tissue may react differently and require different amounts of strain for each of the specific tissue types to ensure a positive surgical outcome.

Compression is defined as the percent change in tissue thickness as shown in the following equation:

$$\varepsilon = \frac{h_f - h_i}{h_i}$$

Where ($\varepsilon$) is the strain, ($h_i$) is the initial tissue thickness, and ($h_f$) is the final tissue thickness after compression. Thus, depending on the original thickness of tissue various different strains can be applied to the tissue depending on the tissue type to ensure a positive surgical outcome. In one embodiment, a minimum amount of strain can be required to promote hemostasis, as well as, heal the tissue.

Figure 9:
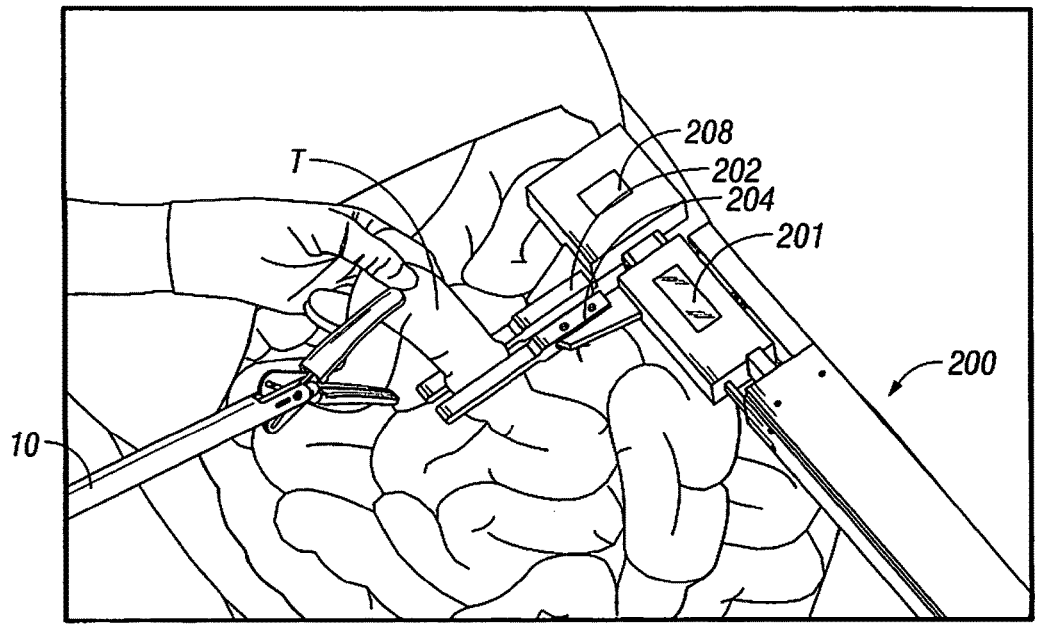
FIGS. 9 and 10 shown the caliper device of FIG. 8 determining the initial tissue thickness and the hemostasis thickness of the tissue.

Referring now to FIG. 9, in this embodiment, the caliper device 200 measures an initial thickness of the tissue T. In one embodiment where animal small intestine tissue T is being operated upon, the method has the step of determining an initial thickness of the aligned two tissue sections as shown in FIG. 9. One should appreciate that any desired units shown on the display 201 may be centimeters, or inches so long as the measurements are taken in the subsequent procedures with the same consistent units.

Figure 10:
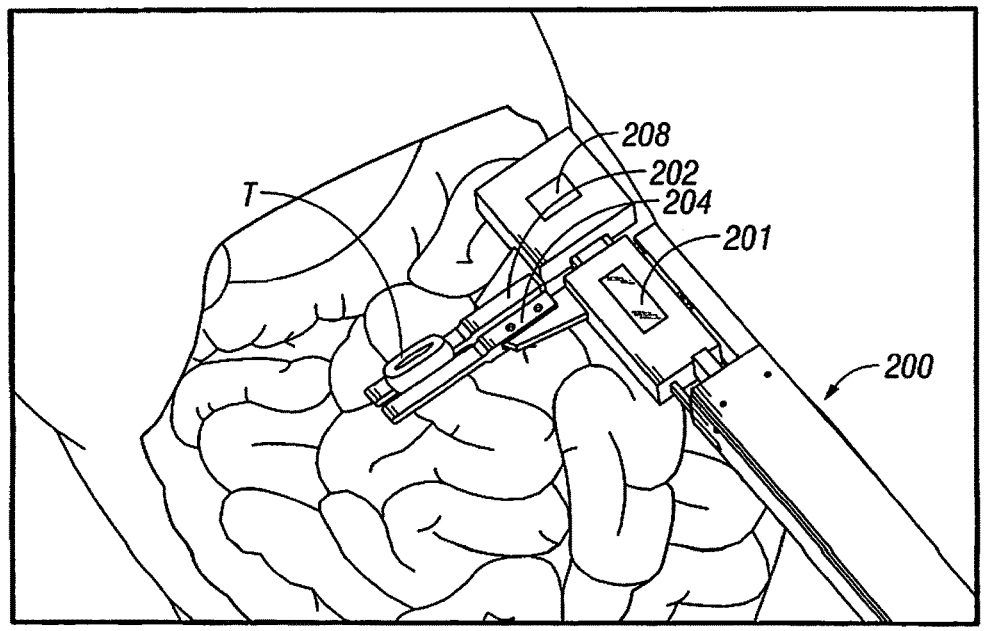

Referring now to FIG. 10, the method next has the step of compressing the two tissue sections together using the caliper device 200 from the initial thickness to a compressed thickness to determine a second thickness. The second thickness is a thickness at the occurrence of some physiological event. In one embodiment, the physiological event is a hemostasis or the stoppage of bleeding from the tissue. This second thickness is measured using the caliper device 200 by slowly releasing the tissue section T from the first and second caliper arms 202, 204 until a visual inspection of the two tissue sections T can be made at a final thickness.

It is envisioned that the final thickness is the recorded thickness where a visual inspection of a physiological response or event occurs. The visual inspection of a physiological response is, in one embodiment, the presence of a fluid, or blood traversing through the tissue. However, the present method is not limited to simply observing a hemostasis of tissue. Examples of other physiological responses include partial hemostasis of the tissue, leakage of a fluid from the tissue, blood leakage from the tissue, or a complete healing of the tissue when the predetermined amount of compression from the device, (or another clamp is applied to the tissue T), or a time period elapsed thereafter.

Figure 10A:
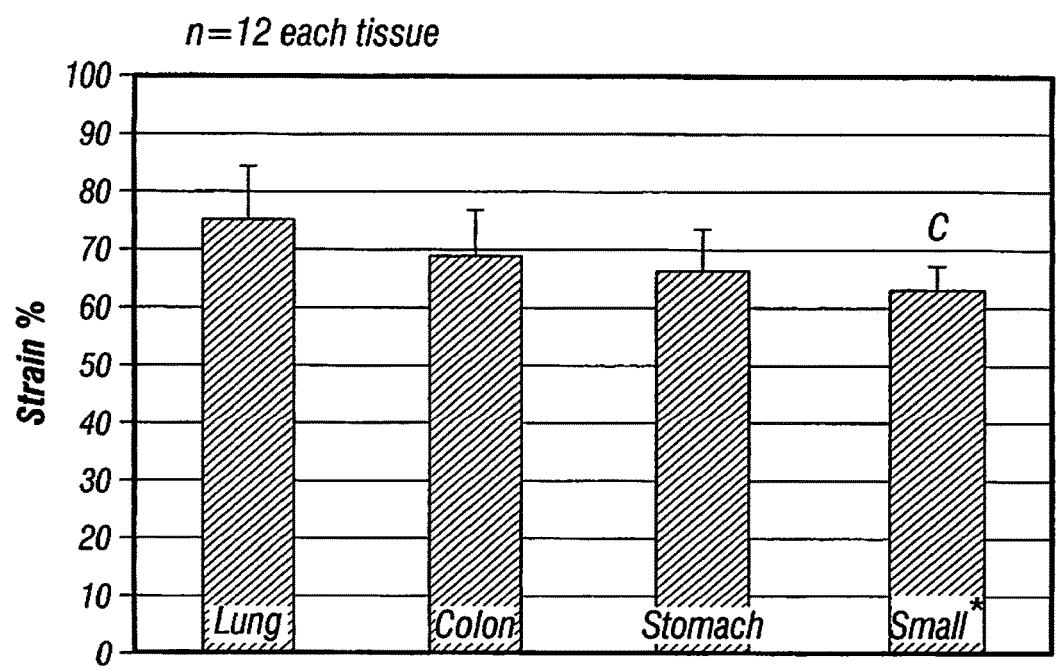
FIG. 10A is a plot of a percentage amount of compressive strain applied to tissue for several different tissue types.

Referring now to FIG. 10A, there is shown a graph of various different strains for several different tissue types. FIG. 10A is derived from the plot of shows strain applied to several different tissue types including lung tissue, colonic tissue, stomach tissue, and small intestinal tissue. FIG. 10A shows the small intestinal plot generally indicated as "small". The values indicate that in this particular non-limiting embodiment the tissue is being compressed. The y-axis shows in FIG. 10A the optimal percentage or amount of compression that is determined from the initial tissue thickness. This percentage thickness is recorded at the point of compression when the presence of blood at the cut edge of the transected tissue was observed in a test study. It is envisioned that to create hemostasis for gastrointestinal tissue a strain range of about 60 to 80 percent is acceptable as multiplied by the initial uncompressed measured thickness. It is further envisioned that to create hemostasis for small intestinal tissue a strain range of about 60 to 70 percent is acceptable. It is envisioned that to create hemostasis for stomach tissue a strain range of about 65 to 75 percent is acceptable. It is also envisioned that to create hemostasis for colonic tissue a strain range of about 70 to 80 percent is acceptable. It should be further appreciated that pulmonary tissue is found to be significantly softer than other tissue types. Because of the specific properties of the pulmonary tissue the percentage of compression required to achieve tissue hemostasis is observed to be greater relative to other tissue types (such as abdominal tissue, or colonic tissue) as shown in FIG. 10A.

It is envisioned that to promote tissue fusion in the sub mucosa section of tissue that a strain range of about 60 to 90 percent is acceptable. Generally, to create hemostasis for all tissue types a strain range of about 60 to 80 percent is acceptable as a general range. This general range is noted to promote a marked improvement to tissue fusion for all tissue types. However, various other factors such as tissue type, and/or tissue disease and the specific pathology of the individual patient must be taken into consideration in view of the general range.

For the purposes of explanation, the two tissue sections T will be discussed in the context of an anastomosis procedure where the two tissue sections T are desired to be joined form a lumen. Care is brought to such a situation so an optimal amount of compression is brought onto the two tissue sections prior to the introduction of a surgical element, such as a stapler, or suture so as to avoid any leakage from the two joined tissue sections which may leak into the another location of the body such as the abdominal cavity.

Thereafter, in one embodiment, a pressurized source of fluid may also be applied to the lumen or the tissue sections that are joined together with the caliper 200. The caliper 200 is slowly released until the amount of blood or plasma escapes from the tissue. The tissue may be further compressed, to determine a thickness at the hemostasis of the tissue. In this manner, the final thickness of the tissue at the physiological response is measured at a peak force, or when the pressurized fluid flow occurs. In this manner, the final thickness of the tissue is recorded at the optimal compression for this particular tissue.

It is envisioned that only an optimal amount of compression is to be used with the various tissue types such as cardiovascular tissue, pulmonary tissue, abdominal tissue, colonic tissue, and/or gastrointestinal tissue. It is also appreciated that at no time does the caliper 200 exceed the optimal amount of compression for a period of time of about twenty minutes.

Based on the optimal final thickness and the initial thickness of tissue, various parameters of the surgical procedure can be determined based on at least the optimal final thickness and the initial thickness of tissue. In one aspect, based on the final thickness of tissue, the surgeon may use a clamping device that can clamp the tissue to the desired final thickness prior to introducing a surgical element through the tissue. In another aspect, based on the final thickness of tissue, the surgeon may use a clamping device that can clamp the tissue to a general range of final thicknesses (during repeated usage) prior to introducing a surgical element through the tissue such as about eighty to eighty five percent of the initial thickness prior to introducing the surgical element.

It is also envisioned that based on the final thickness of tissue, the surgeon may adjust the surgical instrument to compress the tissue to the desired final thickness. In one embodiment, the surgeon may adjust a predetermined tissue gap measured between, for example, an anvil and a cartridge of the stapler 10 shown in FIG. 9 for the application of the surgical element through the tissue. This predetermined tissue gap may be further altered for the optimal tissue compression. In another embodiment, the surgeon may adjust the surgical stapler 10 shown in FIG. 9 to optimize a staple closure height of the stapler 10.

Figure 11:
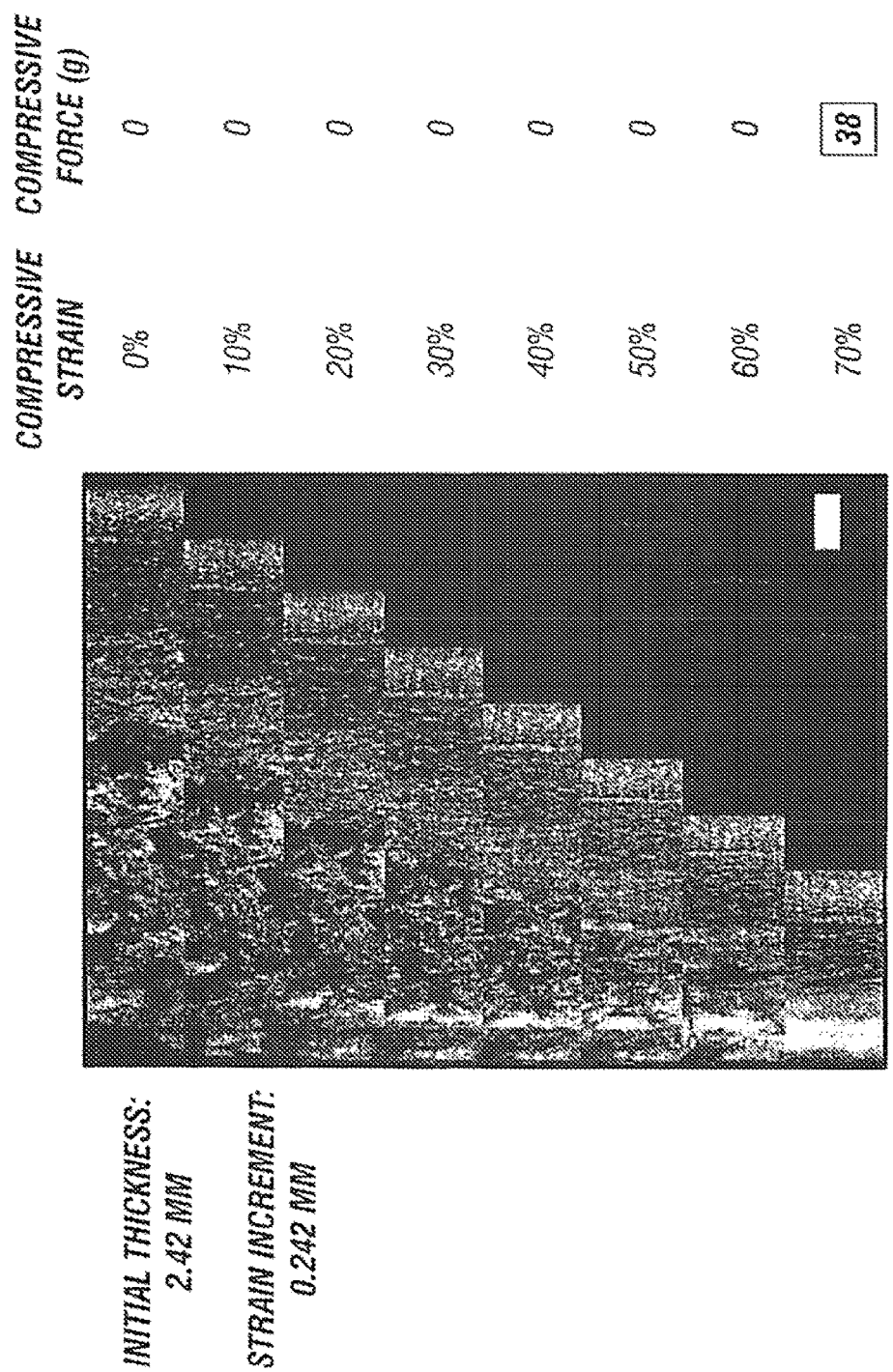
FIG. 11 is an illustration of a tissue section with various sequential degrees of compressive strain applied to the tissue section and the result on the tissue section at each strain increment.
Figure 12A:
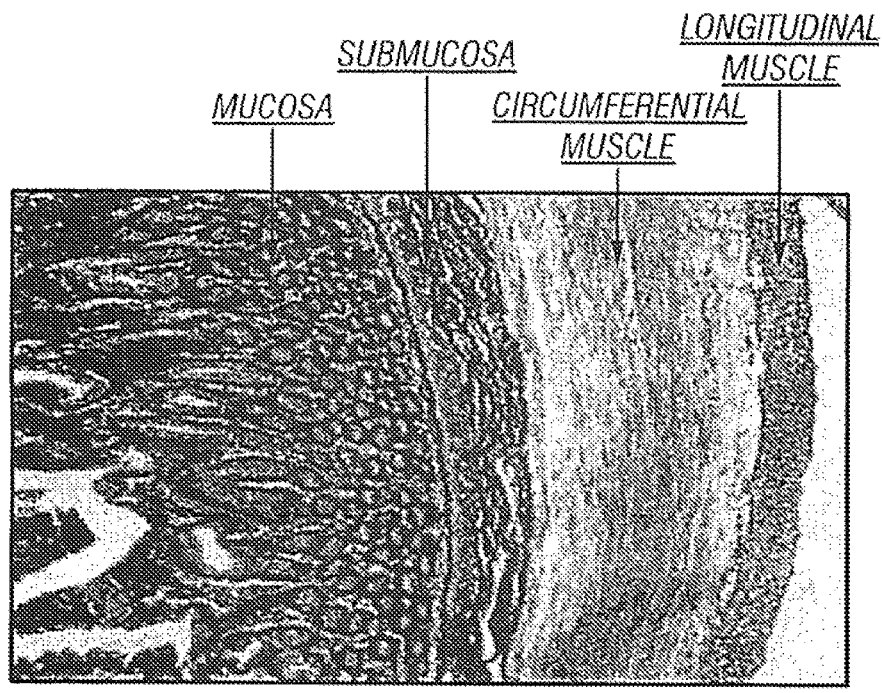
FIGS. 12A and 12B show an example of a small intestine histology with no strain applied and with strain applied to the tissue.
Figure 12B:
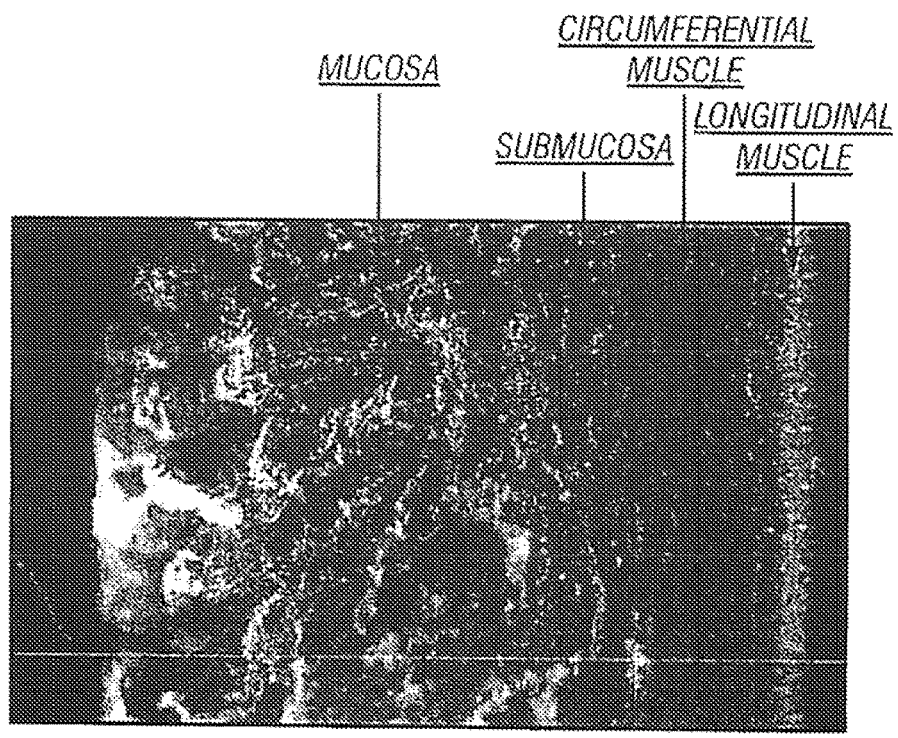

Referring now to FIG. 11, there is shown a compression montage of tissue having an initial thickness of 2.42 mm with a strain increment of 0.242 mm per stage. FIG. 11 shows multiple zones where the compressive strain is increased about ten percent per stage with a strain increment of 0.242 mm per stage until about 70 percent compression is reached. FIG. 12*a* shows the histology of the small intestine. It should be appreciated that the small intestine has a number of tissue layers or a mucosa, sub mucosa, circumferential muscle, and longitudinal muscle. FIG. 12*a* shows the small intestine tissue in the uncompressed or unloaded manner. FIG. 12*b* shows the compressed tissue with the optimal amount of tissue strain.

It is understood that during the course of the optimal tissue strain of the tissue components, several factors come into operation prior to the application of the surgical element through the sections. First, fluid that exists in the tissue will traverse away from the compressed site. Secondly, the tissue in some instances having an amount of tissue therebetween will settle into an even or homogenized tissue resting state. Third, will little or no blood supply to the compressed tissue sections, the tissue begins to soften. It should be appreciated that the tissue is compressed for an optimal period of time, but no longer as compressing the tissue for periods of time in excess of the optimal period of time may lead to necrosis of the tissue. Whereupon, once the compression is released the tissue will not decompress to its initial tissue state for homeostasis.

Figure 13:
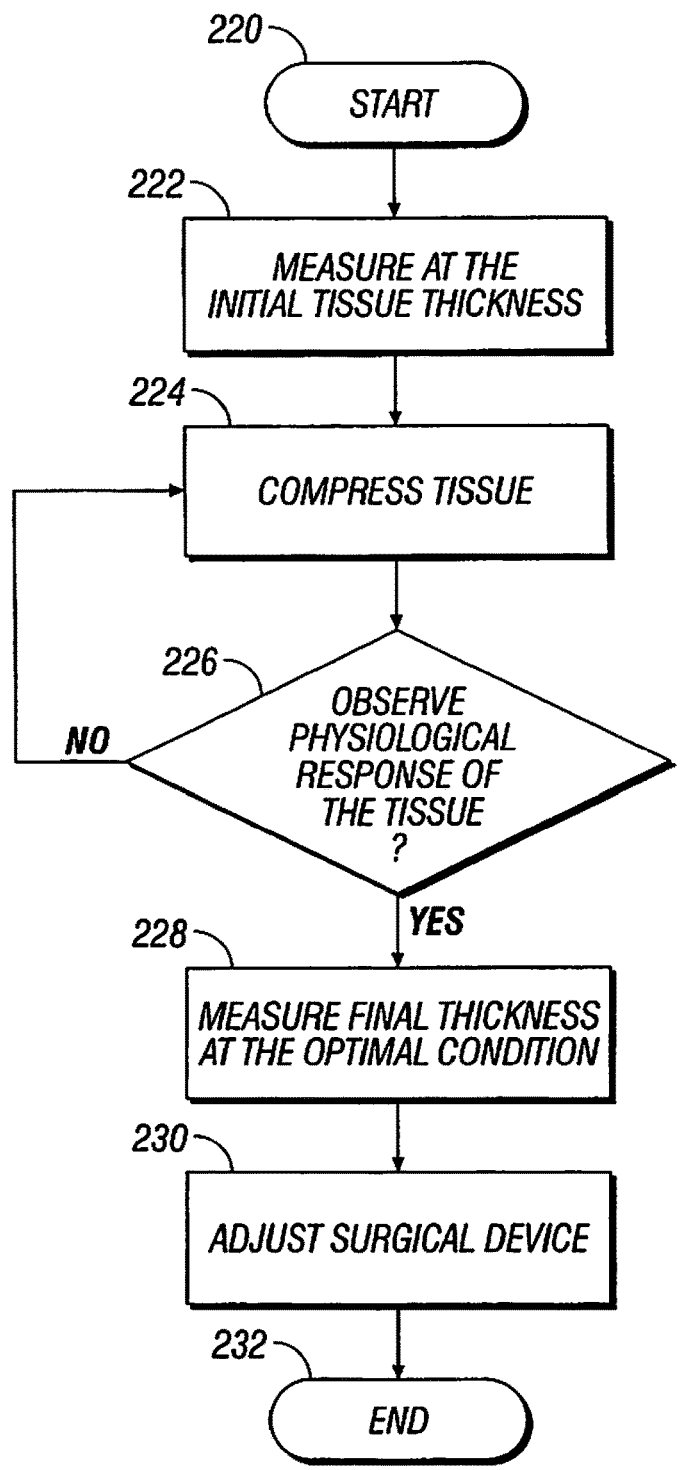
FIG. 13 shows a schematic block diagram according to a method of the present disclosure for measuring an initial tissue thickness of tissue for determining the hemostasis tissue thickness for one or more surgical parameters of the procedure.

Referring now to FIG. 13 there is shown a schematic block diagram according to the present disclosure. The method commences at step 220. Thereafter, the method continues to step 222. At step 222, the method has the step of measuring the initial thickness of the tissue. Thereafter, the method continues to step 224. At step 224, the tissue is compressed. In one embodiment, the tissue is compressed in a stepwise fashion as shown in FIG. 11 in increments. In another embodiment, the tissue may be compressed using the caliper device 200 of FIG. 8 in one step. Thereafter, the method continues to step 226. At step 226, the method reaches a decision block.

Here at step 226, the surgeon observes the physiological response of the tissue at the compression, such as hemostasis of tissue, the healing of the tissue, or leaking of fluid from the tissue to determine whether the optimal amount of compression of the tissue has been reached. If the positive response has been observed at step 226, then the method continues to step 228 where the final thickness at the physiological response is recorded.

Thereafter, the method continues to step 230 where the surgical device is adjusted in a manner consistent with the final tissue thickness. As mentioned, staple size selection can be changed in response to the final tissue thickness, the gap between the surgical stapler and the anvil, or another parameter of the instrument or procedure may be altered. At step 226, where the method reaches the decision block and the surgeon does not observe any of the enumerated physiological response(s) from the tissue at the compression, this is indicative that the optimal amount of compression of the tissue has not been reached. If the negative response has been observed at step 226, then the method continues back to step 224 to further compress the tissue at the next incremental amount such as measured in millimeters. Once the instrument is adjusted, the method terminates at step 232.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments.

What is claimed is:

1. A method for determining an optimal compression of tissue to apply a surgical element to the tissue, the method comprising:
    measuring an initial thickness of the tissue before applying the load to the tissue with the moveable platen;
    applying a load to the tissue with a moveable platen;
    measuring a velocity of the moveable platen in response to the load applied to the tissue; and
    providing an audible signal when the velocity of the moveable platen reaches a predetermined velocity which is indicative that about eighty percent tissue compression has been achieved representing optimal compression.

2. The method according to claim 1, further comprising varying the predetermined velocity in response to a distance between the moveable platen and a stationary platen.

3. The method according to claim 1, further comprising modulating the surgical instrument in response to the signal and the measured velocity of the moveable platen.

4. The method according to claim 3, wherein modulating the surgical instrument includes changing a staple size.

5. The method according to claim 3, wherein modulating the surgical instrument includes changing a size of a gap between a stapler cartridge and an anvil.

6. The method according to claim 1, wherein measuring the initial thickness of the tissue includes determining a distance between the moveable platen and a stationary platen when the moveable platen contacts the tissue.

7. The method according to claim 1, wherein measuring the initial thickness of the tissue includes determining the thickness of the tissue with a caliper.

8. The method according to claim 1, further comprising determining when the tissue thickness reaches a predetermined compression from the initial thickness, and wherein the predetermined compression from the initial thickness is a predetermined distance threshold.

\* \* \* \* \*